United States Patent
Oonishi et al.

(10) Patent No.: US 10,358,638 B2
(45) Date of Patent: Jul. 23, 2019

(54) METHOD OF PRODUCING 1,5-PENTADIAMINE USING LYSINE DECARBOXYLASE MUTANT HAVING IMPROVED THERMAL STABILITY

(71) Applicant: AJINOMOTO CO., INC., Tokyo (JP)

(72) Inventors: Fumito Oonishi, Kanagawa (JP); Yasuhiro Mihara, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/259,179

(22) Filed: Sep. 8, 2016

(65) Prior Publication Data

US 2016/0376580 A1 Dec. 29, 2016

Related U.S. Application Data

(63) Continuation of application No. PCT/JP2015/057211, filed on Mar. 11, 2015.

(30) Foreign Application Priority Data

Mar. 11, 2014 (JP) ................................ 2014-047719

(51) Int. Cl.
  *C12N 9/88* (2006.01)
  *C12P 13/00* (2006.01)
  *C12Q 1/6876* (2018.01)

(52) U.S. Cl.
  CPC .............. *C12N 9/88* (2013.01); *C12P 13/001* (2013.01); *C12Q 1/6876* (2013.01); *C12Y 401/01018* (2013.01)

(58) Field of Classification Search
  CPC . C12N 9/88; C12Y 401/01018; C12P 13/001; C12Q 1/6876
  See application file for complete search history.

(56) References Cited

U.S. PATENT DOCUMENTS

| 2013/0079486 A1 | 3/2013 | Hidesaki et al. |
| 2015/0132808 A1 | 5/2015 | Mochizuki et al. |

FOREIGN PATENT DOCUMENTS

| EP | 2543736 A1 | 1/2013 |
| EP | 2806026 A1 | 11/2014 |
| JP | 2008-193899 A | 8/2008 |
| JP | 2002-223770 A | 8/2013 |
| WO | WO2011/108473 A1 | 9/2011 |
| WO | WO2013/108859 A1 | 7/2013 |
| WO | WO2013/108860 A1 | 7/2013 |
| WO | WO2013/151139 A1 | 10/2013 |

OTHER PUBLICATIONS

Ward et al, 2011 UniProt Acc# E5YIJ5. Alignment with SEQ ID No. 1.*
Qian, Z.-G., et al., "Metabolic Engineering of *Escherichia coli* for the Production of Cadaverine: A Five Carbon Diamine," Biotechnol. Bioeng. 2011;108(1):93-103.
Database UniProt [Online], Jul. 28, 2009, "SubName: Full=Orn/Lys/Arg decarboxylase family protein, putative," XP055390838, retrieved from EBI accession No. UNIPROT:C5B7S8 on Jul. 14, 2017, Database accession No. C5B7S8.
Database UniProt [Online], May 18, 2010, "SubName: Full=Lysine decarboxylase, inducible," XP055390843, retrieved from EBI accession No. UNIPROT:D4F9N3 on Jul. 14, 2017, Database accession No. D4F9N3.
Database seed [Online], Mar. 19, 2013, XP055390847, retrieved from EBI Database accession No. dig 1126217.3.peg.985 on Jul. 14, 2017.
Supplementary European Search Report for European Patent App. No. 15761936.2 (dated Jul. 28, 2017).
Hartmann, T., et al., "A Chloroplast-Localized Lysine Decarboxylase of Lupinus Polyphyllus," FEBS Letters 1980;115(1):35-38.
Kim, H. S., et al., "Purification and Characterization of Monomeric Lysine Decarboxylase from Soybean (*Glycine max*) Axes," Arch. Biochem. Biophys. 1998;354(1):40-46.
Pelosi, L. A., et al., "Lysine Decarboxylase Activity and Alkaloid Production in Heimia Salicifolia Cultures," Phytochem. 1986;25(10):2315-2319.
International Search Report for PCT Patent App. No. PCT/JP2015/057211 (dated Jun. 16, 2015).

* cited by examiner

*Primary Examiner* — Sheridan Swope
(74) *Attorney, Agent, or Firm* — Cermak Nakajima & McGowan LLP; Shelly Guest Cermak

(57) ABSTRACT

The present invention provides methods for producing 1,5-pentamethylenediamine ("1,5-PD") efficiently in a manner suitable for an actual production. Specifically, the present invention provides a method of producing 1,5-pentamethylenediamine including allowing a lysine decarboxylase mutant to act on L-lysine and/or a salt thereof, wherein said lysine decarboxylase mutant has an amino acid sequence selected from the group consisting of:

(a) the amino acid sequence of SEQ ID NO:1,
(b) an amino acid sequence of SEQ ID NO: 1, but having one or several amino acid residue substitutions, deletions, insertions or additions, and
(c) an amino acid sequence having 90% or more identity to the amino acid sequence of SEQ ID NO:1, and having a lysine decarboxylation activity, and wherein said lysine decarboxylase has improved thermal stability.

16 Claims, 1 Drawing Sheet
Specification includes a Sequence Listing.

METHOD OF PRODUCING 1,5-PENTADIAMINE USING LYSINE DECARBOXYLASE MUTANT HAVING IMPROVED THERMAL STABILITY

This application is a Continuation of, and claims priority under 35 U.S.C. § 120 to, International Application No. PCT/JP2015/057211, filed Mar. 11, 2015, and claims priority therethrough under 35 U.S.C. § 119 to Japanese Patent Application No. 2014-047719, filed Mar. 11, 2014, the entireties of which are incorporated by reference herein. Also, the Sequence Listing filed electronically herewith is hereby incorporated by reference (File name: 2016-09-08T_US-549_Seq_List; File size: 11 KB; Date recorded: Sep. 8, 2016).

BACKGROUND OF THE INVENTION

Field of the Invention

The present invention relates to a method of producing 1,5-pentadiamine using a lysine decarboxylase mutant having an improved thermal stability, and the like.

Brief Description of the Related Art 1,5-Pentadiamine (also referred to as cadaverine and abbreviated as "1,5-PD") is a substance, demand for which is expected to rise for uses such as a resin raw material for polyamide resins, or as a pharmaceutical intermediate. 1,5-PD can be produced from a non-petroleum based material, and thus also is industrially attractive in terms of reducing the environmental load.

Lysine decarboxylase (LDC) is utilized in methods of biologically producing 1,5-PD. LDC is an enzyme that catalyzes formation of 1,5-PD and $CO_2$ from lysine. For example, methods of producing 1,5-PD using LDC have been reported, wherein the LDC is derived from *Escherichia coli* (JP patent application laid-open Publication No. JP2002-223770, Patent Literature 2: JP patent application laid-open Publication No. JP2008-193899, and International publication WO2013/180859), sun opener (*Heimia salicofolia*) (Pelosi, L. A. et al., Phytochemistry 25, 2315-2319 (1986)), soybean (*Glycine max*) (Kim, H. S. et al., Arch. Biochem. Biophys. 354, 40-46 (1998)) or lupin (*Lupinus polyphyllus*) (Hartmann T. et al., FEBS Letters, 115, 35-38 (1980)).

SUMMARY OF THE INVENTION

LDC is a non-secretory protein. Therefore, when expressing LDC in a microorganism, 1,5-PD cannot be produced efficiently because the lysine added to the culture medium is not absorbed into the microorganism, and so cannot react with the LDC present inside the microorganism. In order to react the LDC present inside the microorganism with the lysine added to the culture medium, the microorganism must be disrupted. However, it is not practical to disrupt the microorganism in large amounts due to considerable labor and cost. Thus, it is an aspect of the present invention to produce 1,5-PD in a more efficient manner, which is suitable for actual production.

It has been found that 1,5-PD can be efficiently formed from lysine without disruption of the microorganism when thermally stable LDC is used and the microorganism is heated. The present invention also describes a mutated LDC that has higher thermal stability, which can be used in such a method.

It is an aspect of the present invention to provide a method of producing 1,5-pentamethylenediamine, comprising allowing a lysine decarboxylase mutant to act on L-lysine and/or a salt thereof wherein said lysine decarboxylase has an amino acid sequence selected from the group consisting of:

(a) the amino acid sequence of SEQ ID NO:1, (b) an amino acid sequence of SEQ ID NO: 1, but having one or several amino acid residue substitutions, deletions, insertions or additions, and (c) an amino acid sequence having 90% or more identity to the amino acid sequence of SEQ ID NO:1; and wherein said lysine decarboxylase mutant has an additional substitution of an amino acid residue selected from the group consisting of Val at position 3 or a position corresponding to position 3, Ala at position 590 or a position corresponding to position 590, Glu at position 690 or a position corresponding to position 690, and combinations thereof, wherein said lysine decarboxylase mutant has improved thermal stability as compared to a lysine decarboxylase without said additional substitution.

It is an additional aspect of the present invention to provide the method as described above, wherein said method further comprises using a microorganism that has been transformed with an expression vector comprising a polynucleotide encoding the lysine decarboxylase mutant.

It is an additional aspect of the present invention to provide the method as described above, wherein said additional substitution is a substitution of Val at position 3 or a position corresponding to position 3 with Ile, a substitution of Ala at position 590 or a position corresponding to position 590 with Thr, or a substitution of Glu at position 690 or a position corresponding to position 690 with Gly.

It is an additional aspect of the present invention to provide the method as described above, wherein the method further comprises heating the microorganism.

It is an additional aspect of the present invention to provide the method as described above, wherein the microorganism is *Escherichia coli*.

It is an aspect of the present invention to provide a lysine decarboxylase mutant having an amino acid sequence selected from the group consisting of:

(a) the amino acid sequence of SEQ ID NO:1, (b) an amino acid sequence of SEQ ID NO: 1, but having one or several amino acid residue substitutions, deletions, insertions or additions, and (c) an amino acid sequence having 90% or more identity to the amino acid sequence of SEQ ID NO:1, and wherein said lysine decarboxylase mutant has an additional substitution of an amino acid residue selected from the group consisting of Val at position 3 or a position corresponding to position 3, Ala at position 590 or a position corresponding to position 590, and Glu at position 690 or a position corresponding to position 690, and combinations thereof, and wherein said lysine decarboxylase mutant has improved thermal stability as compared to a lysine decarboxylase without said additional substitution.

It is an additional aspect of the present invention to provide the lysine decarboxylase mutant as described above, wherein said additional substitution is a substitution of Val at position 3 or a position corresponding to position 3 with Ile, a substitution of Ala at position 590 or a position corresponding to position 590 with Thr, or a substitution of Glu at position 690 or a position corresponding to position 690 with Gly.

It is a further aspect of the present invention to provide a polynucleotide encoding the lysine decarboxylase mutant as described above.

It is a further aspect of the present invention to provide an expression vector comprising the polynucleotide as described above.

It is a further aspect of the present invention to provide a microorganism comprising the expression vector as described above.

It is a further aspect of the present invention to provide the microorganism as described above, wherein the microorganism is *Escherichia coli*.

The method of the present invention can efficiently produce 1,5-PD in a manner more suitable for actual production.

DESCRIPTION OF THE PREFERRED EMBODIMENTS

Figure 1:
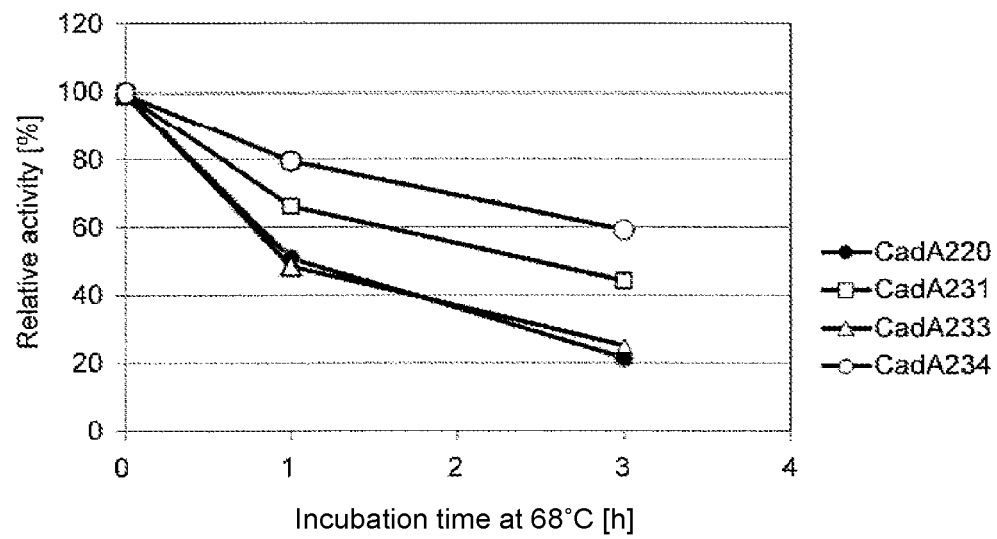
FIG. 1 shows the remaining activity of a wild-type enzyme and mutated enzymes after incubation at 68° C. CadA220: wild-type enzyme, CadA231: V3I mutant, CadA233: A590T mutant, and CadA234: V3I/A590T mutant.

The present invention provides a method of producing 1,5-pentamethylenediamine by reacting L-lysine and/or a salt thereof with a mutated lysine decarboxylase.

The mutated lysine decarboxylase has improved thermal stability. Specifically, the mutated lysine decarboxylase includes a protein that has one or more amino acid residue mutations that improve the thermal stability, and includes a protein having an amino acid sequence of the amino acid sequence of SEQ ID NO:1, an amino acid sequence of SEQ ID NO: 1, but which has one or several amino acid residue substitutions, deletions, insertions or additions, or an amino acid sequence having 90% or more identity to the amino acid sequence of SEQ ID NO:1.

The mutated lysine decarboxylase has lysine decarboxylation activity, even when mutated. The lysine decarboxylation activity can mean an activity to convert lysine into 1,5-PD.

The present invention also provides a lysine decarboxylase mutant.

The lysine decarboxylase mutant may be derived from, or be native to, *Escherichia coli*. One or more amino acid residue mutations can be introduced to the native lysine decarboxylase derived from *Escherichia coli* or analogous species thereof. The native lysine decarboxylase can have the amino acid sequence of SEQ ID NO:1, the amino acid sequence of SEQ ID NO: 1, but one that includes one or several amino acid residue substitutions, deletions, insertions or additions, or an amino acid sequence having 90% or more identity to the amino acid sequence of SEQ ID NO:1, as long as the lysine decarboxylase maintains lysine decarboxylase activity. The lysine decarboxylase derived from, or native to, *Escherichia coli* can also be referred to as CadA, and is known to form a decamer composed of monomers having a subunit molecular weight of 81 kDa.

The amino acid sequence can include one or more amino acid residue mutations, such as substitutions, deletions, insertions, and additions. The number of these mutations can be, for example, 1 to 50, 1 to 40, 1 to 30, 1 to 20, 1 to 10, and including e.g., 1, 2, 3, 4 or 5.

The amino acid sequence can have 90% or more amino acid sequence identity to the amino acid sequence of SEQ ID NO:1. The amino acid sequence percent identity may be 92% or more, 95% or more, 97% or more, 98% or more, or 99% or more.

The percent identity of the amino acid sequences can be determined using the algorithm BLAST (Pro. Natl. Acad. Sci. USA, 90, 5873 (1993)) by Karlin and Altschul, and FASTA (Methods Enzymol., 183, 63 (1990)) by Pearson. The program referred to as BLASTP was developed based on the algorithm BLAST (see ncbi.nlm.nih.gov). Thus, the percent identity of the amino acid sequences may be calculated using these programs with default settings. Also, for example, a numerical value obtained by calculating similarity as a percentage at a setting of "unit size to compare=2" using the full length of a polypeptide portion encoded in ORF with the software GENETYX Ver. 7.0.9 from Genetyx Corporation employing Lipman-Pearson method may be used as the identity of the amino acid sequences. The lowest value among the values derived from these calculations may be employed as the identity of the amino acid sequences.

In preparation of an amino acid sequence having one or several amino acid residue substitutions, deletions, insertions or additions in the amino acid sequence of SEQ ID NO:1, and an amino acid sequence having 90% or more identity to the amino acid sequence of SEQ ID NO:1, the positions of amino acid residues to be mutated in the amino acid sequence of SEQ ID NO:1 are understood by a person skilled in the art. For example, mutations can be introduced with reference to an amino acid sequence alignment. Specifically, a person skilled in the art would be able to recognize the correlation between structure and function, since the person can 1) compare the amino acid sequences of multiple homologs (known lysine decarboxylase sequences), 2) clarify regions that are relatively conserved and regions that are not relatively conserved, and then 3) predict regions capable of playing a functionally important role and regions incapable of playing a functionally important role from the regions that are relatively conserved and the regions that are not relatively conserved, respectively. Therefore, the person skilled in the art can determine the amino acid sequences that can be introduced with one or more amino acid residue mutations that improve thermal stability.

In preparation of an amino acid sequence having one or several amino acid residue substitutions, deletions, insertions or additions in the amino acid sequence of SEQ ID NO:1, and an amino acid sequence having 90% or more identity to the amino acid sequence of SEQ ID NO:1, when an amino acid mutation is introduced to the amino acid sequence of SEQ ID NO:1 and the amino acid mutation is a substitution, the substitution may be a conservative substitution. The term "conservative substitution" refers to substitution of an amino acid residue with another amino acid residue having a similar side chain. Families of the amino acid residues having the similar side chain are well-known in the art. Examples of such families may include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a nonpolar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a hydroxyl group (e.g., alcoholic, phenolic)-containing side chain (e.g., serine, threonine, tyrosine), and amino acids having a sulfur-containing side chain (e.g., cysteine, methionine). The amino acid having a non-charged polar side chain and the amino acid having a non-polar side chain may be collectively referred to as a neutral amino acid. The conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

In the lysine decarboxylase mutant, at least one amino acid residue is mutated so as to improve a thermal stability. Examples of the amino acid residue mutations include substitution, deletions, additions and insertions. The amino acid residue to be mutated can be L-alanine (A), L-asparagine (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H) or L-lysine (K) that is naturally occurring L-α-amino acid, or glycine (G). When the mutation is a substitution, addition or insertion, the amino acid residue to be substituted, added or inserted is the same as the amino acid residue to be mutated as described above. Hereinafter, L and α may be abbreviated for description of an amino acid.

The mutated lysine dehydrogenase that improves the thermal stability may be a protein with substitution(s) of one or more amino acid residues such as the Val at position 3 or a position corresponding to position 3, the Ala at position 590 or a position corresponding to position 590, and the Glu at position 690 or a position corresponding to position 690, in the amino acid sequence of SEQ ID NO:1, the amino acid sequence of SEQ ID NO: 1, but that includes one or several amino acid residue substitutions, deletions, insertions or additions, or an amino acid sequence having 90% or more identity to the amino acid sequence of SEQ ID NO:1. The person of ordinary skill in the art can appropriately determine the positions or corresponding positions as described above in SEQ ID NO: 1 as described above. The mutated lysine decarboxylase may include multiple substitutions (e.g., two or three substitutions) at the positions above in combination. The Val at position 3 or a position corresponding to position 3 can be substituted with an isoleucine residue. The Ala at position 590 or a position corresponding to position 590 can be substituted with an amino acid residue having a non-charged polar side chain, such as a threonine residue. The Glu at position 690 or a position corresponding to position 690 can be substituted with a neutral amino acid residue, such as an amino acid residue having a nonpolar side chain, for example, a glycine residue.

The mutated lysine decarboxylase may also have another peptide component, such as a tag moiety, at its C terminus or N terminus. Examples of these other peptide components may include peptide components that make purification of the objective protein easy (e.g., tag moieties such as a histidine tag, Strep-tag II and the like; proteins commonly used for the purification of an objective protein, such as glutathione-S-transferase, a maltose binding protein and the like), peptide components that enhance the solubility of the objective protein (e.g., Nus-tag), peptide components that work as a chaperon (e.g., a trigger factor), and peptide components that have another function or function as a linker domain.

In the method of producing 1,5-PD of the present invention, 1,5-PD is formed from L-lysine and/or a salt thereof by the action of the mutated lysine decarboxylase. The salt of L-lysine may include non-metal salts such as inorganic acid salts (e.g., hydrochloride salts), inorganic base salts (e.g., ammonium salts), organic acid salts (e.g., acetate salts), and organic base salts (e.g., triethylamine salts) as well as metal salts such as alkali metal salts (e.g., sodium salts, potassium salts) and alkali earth metal salts (e.g., calcium salts, magnesium salts).

1,5-PD can be formed using a microorganism transformed with an expression vector that includes a polynucleotide encoding the mutated lysine decarboxylase, such as a transformant. When 1,5-PD is formed using the transformant, a culture conditions for forming 1,5-PD are described herein.

When 1,5-PD is formed using a transformant, the transformant can be heated in order to release the lysine decarboxylase, which is a non-secretory protein, out of the transformant. Examples of the heat treatment may include incubation at temperature of 40° C. or above (e.g., 40° C. to 70° C., or 50° C. to 60° C.) for 10 minutes to 12 hours, 1 to 6 hours, or 1 to 3 hours. The transformant may be heated when it is suspended in broth just after cultivation or resuspended in buffer or the like. When 1,5-PD is formed using the transformant, L-lysine and/or the salt thereof can also be added to the culture medium in order to enhance the yield of 1,5-PD.

The method of producing 1,5-PD may be carried out in the presence of a metal-chelating agent. 1,5-PD can be produced in an iron-containing container such as a metallic fermentation tank containing iron. However, for example, when lysine hydrochloride is used as a substrate, a chloride ion may facilitate elution of the iron ion from the iron-containing container. The lysine decarboxylase composed of the amino acid sequence of SEQ ID No:1 has a property where its enzymatic activity is inhibited by the iron ion. Thus, the iron ion eluted as above may inhibit the enzymatic activity of this lysine decarboxylase. Therefore, the metal-chelating agent can be utilized in order to capture the iron ion that acts as an inhibitor. The metal-chelating agent may be a monodentate-chelating agent or a multidentate-chelating agent as long as it can capture the iron ion, and examples thereof may include polyphosphates [e.g., sodium tripolyphosphate, hexametaphosphoric acid, acidic sodium pyrophosphate, sodium pyrophosphate, tetrasodium pyrophosphate, sodium hexametaphosphate, sodium metaphosphate], aminocarboxylic acids [e.g., ethylenediamine tetraacetic acid (EDTA), 1,2-bis(2-amino-phenoxy)ethane-N,N,N',N'-tetraacetic acid (EGTA), ethylenebis(oxyethylenenitrilo) tetraacetic acid (BAPTA), N-(hydroxyethyl)ethylenediamine triacetic acid (HEDTA), diethylenetriamine pentaacetic acid (DTPA), N-dihydroxyethylglycine (2-HxG), ethylenebis (hydroxyphenyl-glycine) (EHPG), glutamic acid, aspartic acid, glycine, lysine], 1,3-diketones [e.g., acetylacetone, trifluoroacetylacetone, thenoyltrifluoroacetone, ascorbic acid], hydroxycarboxylic acids [e.g., tartaric acid, citric acid, malic acid, gluconic acid, ferulic acid, lactic acid, glucuronic acid], polyamines [e.g., diethylenetriamine, triethylenetriamine], aminoalcohols [e.g., triethanolamine, N-hydroxyethylene-diamine, aminoethylethanolamine (AEEA)], phenols [e.g., disulfopyrocatechol, chromotropic acid], aminophenols [e.g., oxine-sulfonic acid], and Schiff bases

[e.g., disalicylaldehyde 1,2-propylenediimine]. The concentration of the metal-chelating agent can be, for example, 0.1 to 10 mM or 0.5 to 2 mM.

The present invention also provides a polynucleotide encoding the mutated lysine decarboxylase. The polynucleotide may be DNA or RNA, but is preferably DNA.

The mutated lysine decarboxylase can be prepared using a transformant that expresses the mutated lysine decarboxylase, or using a cell free system and the like. The transformant can be produced, for example, by constructing an expression vector and then introducing this expression vector into a host cell.

The expression vector includes the polynucleotide encoding the mutated lysine decarboxylase.

Examples of the expression vector include cell system vectors which express a protein in a host cell, and cell-free system vectors which utilize a protein translation system. Also, the expression vector may be a plasmid, viral vector, phage, integrative vector or artificial chromosome. The integrative vector may be a type of vector in which it is entirely integrated into genome of the host cell. Alternatively, the integrative vector may be a type of vector in which only a part of it, that is, an expression unit that includes the polynucleotide which encodes the mutated lysine decarboxylase, and a promoter operatively linked thereto, is integrated into the genome of the host cell. Furthermore, the expression vector may be a DNA vector or RNA vector.

The expression vector can further include regions encoding a promoter, a terminator, and a drug (e.g., tetracycline, ampicillin, kanamycin, hygromycin, phosphinothricin) resistant gene in addition to the polynucleotide. The expression vector may be a plasmid or an integrative vector. The expression vector may also be a virus vector or a vector for the cell free system. The expression vector may further include a polynucleotide encoding the other peptide component that may be added to the mutated lysine decarboxylase on a 3' terminal side or a 5' terminal side of the polynucleotide of the present invention. Examples of the polynucleotide encoding the other peptide component may include a polynucleotide encoding the peptide component that facilitate the purification of the objective protein as described above, a polynucleotide encoding the peptide component that enhances the solubility of the objective protein as described above, a polynucleotide encoding the peptide component that works as the chaperon, and a polynucleotide encoding the peptide component that has another function or functions as a linker domain. Various expression vectors that include the polynucleotide encoding the other peptide component are available. Therefore, such an expression vector may be utilized for constructing the expression vector. For example, it is possible to utilize an expression vector that includes the polynucleotide encoding the peptide component that facilitates the purification of the objective protein, such as pET-15b, pET-51b, pET-41a, pMAL-p5G, an expression vector that includes the polynucleotide encoding the peptide component that enhances the solubility of the objective protein, such as pET-50b, an expression vector that includes the polynucleotide encoding the peptide component that works as the chaperon, such as pCold TF, and an expression vector that includes the polynucleotide encoding the peptide component that has another function or functions as a linker domain. So that the mutated lysine decarboxylase can be cleaved from the other peptide component added thereto after expression of the protein, the expression vector may include a region encoding a cleavage site that is able to be cleaved by a protease between the polynucleotide encoding the mutated lysine decarboxylase and the polynucleotide encoding the other peptide component.

As a host for expressing the mutated lysine decarboxylase, various prokaryotic cells can be used, including cells derived from *Escherichia* bacteria such as *Escherichia coli*, *Corynebacterium* bacteria (e.g., *Corynebacterium glutamicum*) and *Bacillus* bacteria (e.g., *Bacillus subtilis*) as well as various eukaryotic cells including cells derived from *Saccharomyces* fungi (e.g., *Saccharomyces cerevisiae*), *Pichia* fungi (*Pichia stipitis*) and *Aspergillus* fungi (e.g., *Aspergillus oryzae*). A strain that deletes a certain gene may be used as the host. Examples of the transformant may include transformants possessing an expression vector in cytoplasm and transformants in which an objective gene is introduced on genome.

The transformant can be cultured in medium using a predetermined culture apparatus, such as a test tube, a flask, or a jar fermenter. Culture conditions can be determined appropriately. Specifically, the culture temperature may be 10° C. to 37° C., the pH value may be 6.5 to 7.5, and the culture period of time may be 1 to 100 hours. The cultivation may also be carried out while controlling the dissolved oxygen concentration. In this case, the dissolved oxygen concentration (OD value) in the culture medium is sometimes used as an indicator. Ventilation and/or stirring can be controlled so that the relative dissolved oxygen concentration OD value, when the oxygen concentration in the air is 21%, is not lower than, for example, 1 to 10%, oris not lower than 3 to 8%. The cultivation may be a batch cultivation or a fed-batch cultivation. In the case of the fed-batch cultivation, the cultivation can also be continued by continuously or discontinuously sequentially adding a solution as a sugar source and a solution containing phosphoric acid to the culture medium.

The host to be transformed can be *Escherichia coli*, specifically the strains *Escherichia coli* K12 subspecies *Escherichia coli* JM109 strain, DH5a strain, HB101 strain, BL21 (DE3) strain, and the like. Methods of performing the transformation and methods of selecting the transformant are described in Molecular Cloning: A Laboratory Manual, 3rd edition, Cold Spring Harbor press (2001/01/15), and the like. Hereinafter, a method of producing transformed *Escherichia coli* and producing a certain enzyme will be described specifically by way of example only.

The promoter used for producing an exogenous protein in *E. coli* can generally be a promoter that allows for expression of the polynucleotide. Examples thereof may include potent promoters such as a PhoA, PhoC, T7 promoter, a lac promoter, a trp promoter, a trc promoter, a tac promoter, PR and PL promoters of lambda phage, and a T5 promoter, and the PhoA, PhoC and lac promoters are preferred. For example, pUC (e.g., pUC19, pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30) and derivatives thereof may be used as a vector. A vector from phage DNA may also be utilized as the other vector. Furthermore, an expression vector that includes a promoter and can express an inserted DNA sequence may also be used. The vector may be pUC, pSTV, or pMW.

Also, a terminator that is a transcription terminating sequence may be ligated downstream of the polynucleotide. Examples of such a terminator may include a T7 terminator, an fd phage terminator, a T4 terminator, a terminator of a tetracycline resistant gene, and a terminator of *Escherichia coli* trpA gene.

The vector for introducing the polynucleotide into *Escherichia coli* can be a so-called multicopy-type, and examples thereof may include plasmids which have a replication origin from ColE1, such as pUC-based plasmids, pBR322-based plasmids and derivatives thereof. Here the "derivative" means those in which the modification has been made by substitution, deletion, insertion and/or addition of nucleotide(s).

In order to select the transformant, the vector can have a marker such as an ampicillin resistant gene. Expression vectors having a potent promoter are commercially available, for example, pUC-based (supplied from Takara Bio Inc.), pPROK-based (supplied from Clontech), pKK233-2-based (supplied from Clontech)).

The mutated lysine decarboxylase can be obtained by transforming *Escherichia coli* using the resulting expression vector and culturing this *Escherichia coli*.

Media such as M9/casamino acid medium and LB medium generally used for culturing *Escherichia coli* may be used as the medium. The medium may contain a certain carbon source, nitrogen source, and coenzyme (e.g., pyridoxine hydrochloride). Specifically, peptone, yeast extract, NaCl, glucose, $MgSO_4$, ammonium sulfate, potassium dihydrogen phosphate, ferric sulfate, manganese sulfate, and the like may be used. In addition, the conditions for cultivation and production can be appropriately selected depending on the chosen marker, promoter, vector, and host.

The mutated lysine decarboxylase can be recovered by the following methods and the like. The mutated lysine decarboxylase can be obtained as a disrupted or lysed product by collecting the transformant and subsequently disrupting (e.g., sonication or homogenization) or lysing (e.g., treatment with lysozyme) the microbial cells. The mutated lysine decarboxylase can be obtained by subjecting such a disrupted or lysed product to techniques such as extraction, precipitation, filtration, and column chromatography. Alternatively, collection of the mutated lysine decarboxylase can be performed after the transformant is subjected to heat treatment as described above.

EXAMPLES

Subsequently, the present invention will be described in more detail with reference to the following non-limiting examples.

Example 1: Cloning of Lysine Decarboxylase Gene (cadA) Derived from *Escherichia coli*, Introduction of Mutation, and Screening of Mutant Having Improved Thermal Stability (1) Cloning of cadA Gene and Construction of Expression Library of Mutated Lysine Decarboxylase (CadA)

A DNA fragment including a lysine decarboxylase gene (cadA) was amplified by PCR method using genomic DNA of *Escherichia coli* W3110 (ATCC39936) as a template according to the method described in Example 1 in JP patent application laid-open Publication No. 2008-193899. This fragment was ligated to a modified acid phosphatase promoter derived from genus *Enterobacter* at a XbaI-PstI site in the high-expression plasmid pUC19 (Takara Bio Inc.) and designated pCadA220.

*Escherichia coli* XL1-Red competent cells (Agilent Technologies) used for introduction of random mutation were transformed with pCadA220. The resulting transformants were inoculated to 3 mL of LB medium containing 100 µg/mL of ampicillin, and cultured at 30° C. for 24 hours. Plasmids in which the random mutation had been introduced were collected from these microbial cells, and then *Escherichia coli* JM109 was transformed with these plasmids. The resulting transformants were plated on LB agar medium containing 100 µg/mL of ampicillin to construct a library expressing mutated CadA.

(2) Acquisition of Mutants Having Improved Thermal Stability

A colony of each transformant in which the mutated lysine decarboxylase had been introduced was picked up, inoculated to 1 mL of the LB medium containing 100 µg/mL of ampicillin, and cultured at 30° C. for 24 hours. 18 µL of 100 mM 2-(N-morpholino) ethanesulfonic acid (MES)-NaOH buffer (pH6.0) and 2.7 µL of FastBreak cell lysis reagent (Promega) were added to 10 µL of this cultured medium, which was then incubated at 37° C. for 30 minutes to lyse the microbial cells. Then, this lysate solution was heated up to 65° C. and incubated for 2 hours. After this heat treatment, 190 µL of a reaction solution (pH 5.5) containing 10 g/L of lysine hydrochloride, 21.3 g/L (100 mM) of MES, 26.5 mg/L of Pyridoxal-5'-phosphate (PLP) and 20 mg/L of Bromocresol purple was added and reacted at 37° C. for 40 minutes. The wild-type enzyme is inactivated and a decarboxylation reaction does not occur under these conditions. More abundant formation of 1,5-PD and retention of activity as compared to bacteria expressing the wild-type enzyme after treating with heat under the above conditions were used as an indicator. Three candidate strains expressing CadA having improved thermal stability were obtained using this indicator. These transformants of *E. coli* JM109 strain were designated as CadA231, CadA232 and CadA233, respectively.

The activity of the lysine decarboxylase was measured according to the method described in JP patent application laid-open Publication No. 2008-193899. 0.1 mL of a microbial cell suspension or a treated product thereof was added to 1 mL of a reaction solution containing 100 mM MES-NaOH buffer (pH 6.0), 10 g/L (55 mM) of L-lysine hydrochloride and 26.5 mg/L (0.1 mM) of PLP, and then the reaction mixture was incubated at 37° C. for 5 minutes. 0.1 mL of the reaction solution was collected and added to 1 mL of 1% (v/v) phosphoric acid to stop the reaction. Lysine and 1,5-PD were quantified with HPLC by a post column OPA method (S. R. Vale and M. B. Gloria, Journal Of AOAC International (1997) vol. 80, p. 1006-1012) or a method of quantifying remaining L-lysine using a biosensor BF-5 (Oji Scientific Instruments Co., Ltd.). One unit was defined as an activity that formed 1 µmol of 1,5-PD in one minute under this condition.

Example 2: Analysis of Mutation Site of Mutated Lysine Decarboxylase (CadA) and Evaluation of Stability (1) Analysis of Mutation Site of Mutated Lysine Decarboxylase Plasmids were prepared from the culture medium of the transformants of *E. coli* JM109 retaining the mutated CadA gene obtained in Example 1, and designated as pCadA231, pCadA232 and pCadA233, respectively.

Their nucleotide sequences were determined in 310 Genetic analyzer (ABI) by a Dye Terminator method using DNA Sequencing Kit Dye Terminator Cycle Sequencing Ready Reaction (PERKIN ELMER) to confirm an introduced mutation and a substituted site of a mutated amino acid residue. The nucleotide sequences were analyzed using primers shown in Table 1.

TABLE 1

Nucleotide sequences of primers

| Primer | Nucleotide sequence (SEQ ID) |
|---|---|
| M13 Primer RV | 5'-CAGGA AACAG CTATG AC-3' (SEQ ID NO: 3) |
| cadaf1 | 5'-CTAATA AGATC AAGCA GAC-3' (SEQ ID NO: 4) |
| cadaf2 | 5'-CTGAC CCACC TGATG ATG-3' (SEQ ID NO: 5) |
| cadaf3 | 5'-TGACG TAAAC GAAGA AAC-3' (SEQ ID NO: 6) |
| cadaf4 | 5'-CGAAA TACCT CGACG AAC-3' (SEQ ID NO: 7) |
| cadaf5 | 5'-TGCAT ACCGT CAGGC TGATG-3' (SEQ ID NO: 8) |
| cadar1 | 5'-TCGAA CGCAC GTTTG AAGTC-3' (SEQ ID NO: 9) |
| M13 Primer M4 | 5'-GTTTT CCCAG TCACG AC-3' (SEQ ID NO: 10) |

As a result, the substitutions shown in Table 2 in the mutated enzyme having the improved stability were confirmed.

TABLE 2

Details of substitution of nucleotide residues and amino acid residues

| Plasmid name | Substitution of nucleotide residue | Amino acid residue Wild-type (codon) | Amino acid residue Mutant-type (codon) |
|---|---|---|---|
| pCadA220 | Wild-type enzyme | — | — |
| pCadA231 | G7A | 3 Val (GTT) | Ile (ATT) |
| pCadA232 | A1768G | 690 Glu (GAA) | Gly (GGA) |
| pCadA233 | G2069A | 590 Ala (GCT) | Thr (ACT) |

(2) Evaluation of Stability of Mutated Lysine Decarboxylase

Each transformant was inoculated to 50 mL of L medium in a 500 mL Sakaguchi flask containing 100 µg/mL of ampicillin and cultured with shaking at 30° C. for 16 hours. Microbial cells were collected from the cultured medium by centrifugation, washed once with saline, subsequently suspended in 5 mL of 100 mM potassium phosphate buffer (pH 7.0), and disrupted by sonication at 4° C. for 20 minutes. An insoluble fraction was removed by centrifuging the lysate solution at 8,000 rpm for 10 minutes to prepare a cell free extract.

The resulting cell free extract was diluted 20 fold with 100 mM MES-NaOH buffer (pH 6.0). This crude enzyme solution was incubated at 65° C., and its remaining activity after 3 and 5 hours was measured by the method described in Example 1. As a result, the activity in the crude enzyme solution from the strain expressing the mutated enzyme before incubation was almost the same as that from the strain expressing the wild-type enzyme (Table 3). After incubation at 65° C. for 5 hours, the remaining activity of the wild-type enzyme was reduced by half, but the remaining activity of the obtained mutated enzyme was higher (Table 3), indicating that the thermal stability was improved.

TABLE 3

Remaining activity of each enzyme after incubation at 65° C.

| Plasmid name | Substitution of nucleotide residue | Activity before heating* | Incubation at 65° C. for 3 h* | Incubation at 65° C. for 5 h* |
|---|---|---|---|---|
| pCadA220 | Wild-type enzyme | 697 (100%) | 413 (59.2%) | 360 (51.6%) |
| pCadA231 | V3I | 678 (100%) | 532 (78.4%) | 463 (68.2%) |
| pCadA232 | E690G | 678 (100%) | 500 (86.3%) | 415 (71.7%) |
| pCadA233 | A590T | 632 (100%) | 426 (67.4%) | 344 (54.4%) |

*Units/mL

Example 3: Construction of Combined Combination Mutant and Evaluation of its Stability A combination mutant for increasing the amount of expressed CadA was constructed using QuikChange™ Site-Directed Mutagenesis Kit (Stratagene). A mutation to alter from Val (GTT) to Ile (AAT) at position 3 was introduced using the plasmid pCadA233 as the template and using oligonucleotides v3i_r (5'-cat gtg att caa tat tgc aat aat gtt cat cta cat tcc tcc tta cg-3'(SEQ ID NO:11)) and v3i_f (5'-cgt aag gag gaa tgt aga tga aca tta ttg caa tat tga atc aca tg-3' (SEQ ID NO:12)) as primers according to a protocol. The nucleotide sequence of the constructed plasmid was determined by the method described in Example 2 to confirm that the objective mutation had been introduced, and this plasmid was designated as pCadA234. An outline of the plasmids including the polynucleotide encoding the mutated enzyme is shown in Table 4. Microbial cells of E. coli JM109/pCadA234 expressing this double mutant CadA234 at high level were cultured to prepare a cell free extract in the same manner as in Example 2. The activity in this cell free extract was 663 U/mL, which was almost the same as that from the strain expressing the wild-type enzyme.

TABLE 4

Outline of plasmids prepared in relation to the present application

| Plasmid name | Parent plasmid | Substitution of amino acid residue |
|---|---|---|
| pCadA220 | Wild-type enzyme | |
| pCadA231 | pCadA220 | V3I |
| pCadA232 | pCadA220 | E690G |
| pCadA233 | pCadA220 | A590T |
| pCadA234 | pCadA223 | V3I/A590T |

The resulting cell free extract was diluted to 20 fold with 0.1 M MES-NaOH buffer (pH 6.0). Each crude enzyme solution was incubated at 68° C., which is a higher temperature than in Example 2, and the remaining activity was measured over time. Results are shown in FIG. 1. After incubation at 68° C. for one hour, the wild-type enzyme was inactivated to 27% while the single mutant enzymes V3I and A590T were inactivated to 47% and 27%, respectively. On the contrary, the double mutant enzyme retained 70% of its activity, and even after 3 hours, still retained about 60% of its activity (FIG. 1). Therefore, it was shown that the double mutation has a synergistic effect and further improved the thermal stability.

Example 4: Heat Treatment of Strain Expressing Mutated Lysine Decarboxylase

Microbial cells of E. coli JM109/pCadA220 and E. coli JM109/pCadA234 carrying the wild-type CadA and the double mutant CadA, respectively were cultured in the LB medium. Subsequently, 15 mL of the cultured medium was inoculated into 300 mL of culture medium (25 g/L of glucose, 5 g/L of ammonium sulfate, 2 g/L of potassium phosphate, 1 g/L of magnesium sulfate heptahydrate, 20 mg/L of iron sulfate heptahydrate, 20 mg/L of manganese sulfate pentahydrate, 1 mg/L of thiamine hydrochloride, 0.45 g/L of hydrolyzed soybeans, pH 7.0) in a 500 mL jar fermenter (manufactured by ABLE & Biott Co., Ltd.), and cultured with ventilation at 300 mL/minute while stirring at 250 rpm at 30° C. for 12 hours. Culture media containing 10.1 g/L and 10.9 g/L of microbial cells in terms of dry microbial cell weight were able to be prepared for *E. coli* JM109/pCadA220 and *E. coli* JM109/pCadA234, respectively. For the purpose of improving substrate permeability, the pH value was adjusted to 5.5, and subsequently the culture media were incubated at 55° C. and 60° C., and then the culture media were directly used to measure the activity after the incubation. The results are shown in Table 5.

Since the lysine decarboxylase is expressed within the microbial cell, when the microbial cell is used directly, lysine cannot react with the lysine decarboxylase, and the efficiency of a decarboxylation reaction is very poor. Any of the cultured media after incubation at 60° C. for 3 hours could be used for the enzymatic reaction. However, the wild-type enzyme was inactivated during the incubation when heated excessively. The mutated enzyme having the improved thermal stability could stably keep its activity even when using conditions where the wild-type enzyme was easily inactivated as shown in Example 2. When the microbial cells carrying such a mutated enzyme were used, efficient treatment in a short period of time was possible. This has shown that the mutated enzyme not only can act at higher temperature upon reaction but also can be easily used when the microbial cell is directly used.

TABLE 5

| | Heat treatment | Physical treatment | Enzyme activity (units/ml), and Relative activity(%) | |
|---|---|---|---|---|
| | | | pCadA220 | pCadA234 |
| 1 | No heat | None | 17.5 (1.9%) | 16.0 (2.1%) |
| 2 | treatment | Disruption | 914 (100%) | 770 (100%) |
| 3 | Incubation at | None | 246 (26.9%) | 475 (61.7%) |
| 4 | 55° C. for 1 h | Disruption | 819 (89.6%) | 758 (98.4%) |
| 5 | Incubation at | None | 375 (41.0%) | 601 (78.0%) |
| 6 | 55° C. for 3 h | Disruption | 730 (79.9%) | 659 (85.5%) |
| 7 | Incubation at | None | 282 (30.9%) | 426 (55.3%) |
| 8 | 60° C. for 1 h | Disruption | 798 (87.3%) | 754 (97.9%) |

Example 5: Inhibition of Enzyme Activity by Iron Ion and Effect of the Addition of a Chelating Agent Cell free extracts were prepared from the strain expressing wild-type CadA and the strain overexpressing double mutant CadA, respectively in the same manner as in Examples 2 and 3. Using the resulting cell free extract, iron sulfate heptahydrate (Nacalai Tesque Inc.) at a final concentration of 5.65 mg/L (2 mM) was added to the composition shown in Example 1, and an inhibitory effect was measured. Meanwhile, inhibition of the lysine decarboxylase derived from *E. coli* by iron ion has not been previously reported, but the activity of both the wild-type enzyme and the mutated enzyme was inhibited to 46.8% and 64.7%, respectively of the activity when no iron ion was added by the addition of 2 mM iron ion, as shown in Table 6.

Then, disodium dihydrogen ethylenediaminetetraacetate (EDTA, Nacalai Tesque Inc.) at a final concentration of 1 to 5 mM was added to the reaction solution containing the iron ion, and the effect of the addition was examined. The inhibition by the addition of the iron ion was restored by the addition of the chelating agent EDTA, as shown in Table 6.

TABLE 6

| | | | Enzyme activity (units/ml) | |
|---|---|---|---|---|
| | FeSO$_4$ | EDTA | pCadA220 | pCadA234 |
| 1 | None | None | 850 | 685 |
| 2 | 2 mM | None | 398 | 443 |
| 3 | 2 mM | 0.5 mM | 827 | 677 |
| 4 | 2 mM | 1 mM | 856 | 680 |
| 5 | 2 mM | 2 mM | 821 | 677 |
| 6 | 2 mM | 4 mM | 840 | 672 |
| 7 | 2 mM | 5 mM | 832 | 669 |
| 8 | None | 2 mM | 840 | 677 |

Example 6: Lysine Decarboxylation Reaction in the Presence of Chelating Agent

In the same manner as in Example 4, microbial cells of *E. coli* JM109/pCadA234 (double mutant expressing CadA at high level) were cultured, the cultured medium was prepared, and after completing the cultivation, incubated at 60° C. for one hour. The activity after incubation was measured, and the cultured medium was diluted so that the enzyme activity became 380 units/mL. 30 mL of this cultured medium containing the enzyme was added to 270 mL of a reaction solution containing 250 g/L of lysine hydrochloride (Ajinomoto Co., Ltd.), 26.5 mg/L of pyridoxal phosphate, 27.8 mg/L (0.1 mM) of iron sulfate heptahydrate and 111.6 mg/L (0.3 mM) of disodium dihydrogen ethylenediaminetetraacetate (EDTA), and the mixture was reacted at 37° C. for 16 hours. No EDTA was added in a control reaction. The pH value was 5.3 when the reaction was started, and elevated with progress of the reaction, but was kept at 7.0 by adding 30% (v/v) sulfuric acid when the pH value reached 7.0.

Figure 2:
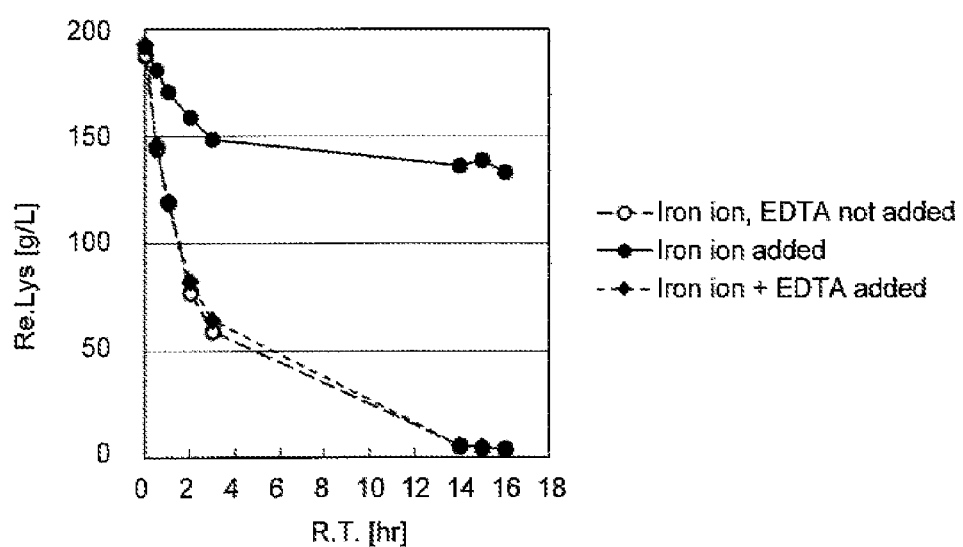
FIG. 2 shows the effects of the addition of a chelating agent on production of 1,5-PD using a mutated lysine decarboxylase (V3I/A590T mutant) as shown in Example 6.

The time course of lysine consumption under each reaction condition was shown in FIG. 2. The reaction was inhibited and additionally did not progress in midstream under the condition without the addition of EDTA. On the other hand, when EDTA was added, the inhibition of the reaction is restored and lysine was completely consumed. When EDTA was added, 135 g/L of 1,5-PD was formed and lysine was converted at a yield of 98%. On the other hand, when EDTA was not added, a concentration of 1,5-PD in the reaction solution was eventually 41.8 g/L. The reaction when neither iron ion nor EDTA was added was quite equivalent to the reaction when EDTA was added. When a metal is brought into contact with a solution containing a chloride ion at high concentration, the reaction can be inhibited by an eluted metal ion. However, this model has suggested that the stability of the reaction is improved by the addition of the chelating agent.

<Condition for 1,5-PD Analysis>

Column: Asahipak ODP-50 4E (supplied from Showa Denko K.K.)

Column temperature: 40° C.

Eluent: 0.2 M sodium phosphate (pH 7.7)+2.3 mM sodium 1-octanesulfonate

Flow of eluent: 0.5 mL/min/min

INDUSTRIAL APPLICABILITY

The present invention is useful for a production of 1,5-PD that can be utilized as a resin raw material for polyamide resins or as a pharmaceutical intermediate.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method of producing 1,5-pentamethylenediamine, comprising allowing a lysine decarboxylase mutant to act on L-lysine and/or a salt thereof, wherein said lysine decarboxylase mutant has an amino acid sequence consisting essentially of the amino acid sequence of SEQ ID NO:1; and contains one of the following:
   (i) a substitution of Val at position 3, or
   (ii) a substitution of Val at position 3 and a substitution of Ala at position 590,
   wherein said lysine decarboxylase mutant maintains the lysine decarboxylation activity of a lysine decarboxylase having an amino acid sequence consisting essentially of SEQ ID NO:1 and has improved thermal stability as compared to a lysine decarboxylase having an amino acid sequence consisting essentially of SEQ ID NO:1.

2. The method according to claim 1, wherein said method further comprises using a microorganism that has been transformed with an expression vector comprising a polynucleotide encoding the lysine decarboxylase mutant.

3. The method according to claim 1, wherein said lysine decarboxylase mutant contains a substitution of Val at position 3 with Ile.

4. The method according to claim 2, further comprising heating the microorganism.

5. The method according to claim 2, wherein the microorganism is *Escherichia coli*.

6. A lysine decarboxylase mutant consisting essentially of the amino acid sequence of SEQ ID NO:1, and contains one of the following:
   (i) a substitution of Val at position 3, or
   (ii) a substitution of Val at position 3 and a substitution of Ala at position 590 or a position corresponding to position 590,
   wherein said lysine decarboxylase mutant maintains the lysine decarboxylation activity of a lysine decarboxylase having an amino acid sequence consisting essentially of SEQ ID NO:1 and has improved thermal stability as compared to a lysine decarboxylase having an amino acid sequence consisting essentially of SEQ ID NO: 1.

7. The lysine decarboxylase mutant according to claim 6, wherein said substitution of Val at position 3 is with Ile.

8. A polynucleotide encoding the lysine decarboxylase mutant according to claim 6.

9. An expression vector comprising the polynucleotide according to claim 8.

10. A microorganism comprising the expression vector according to claim 9.

11. The microorganism according to claim 10, wherein the microorganism is *Escherichia coli*.

12. The lysine decarboxylase mutant of claim 6, wherein said lysine decarboxylase mutant consists of a substitution of Val at position 3.

13. The lysine decarboxylase mutant of claim 6, wherein said lysine decarboxylase mutant contains a substitution of Val at position 3 or a position corresponding to position 3, and a substitution of Ala at position 590 or a position corresponding to position 590.

14. The lysine decarboxylase mutant according to claim 12, wherein said substitution of Val at position 3 is with Ile.

15. The lysine decarboxylase mutant according to claim 6, wherein said substitution of Ala at position 590 is with Thr.

16. The lysine decarboxylase mutant according to claim 13, wherein said substitution of Val at position 3 is with Ile, and said substitution of Ala at position 590 is with Thr.

* * * * *

SEQUENCE LISTING

<160> NUMBER OF SEQ ID NOS: 12

<210> SEQ ID NO 1
<211> LENGTH: 715
<212> TYPE: PRT
<213> ORGANISM: Escherichia coli

<400> SEQUENCE: 1

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Asp Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335
```

```
Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 2
<211> LENGTH: 2148
<212> TYPE: DNA
<213> ORGANISM: Escherichia coli
```

<400> SEQUENCE: 2

```
atgaacgtta ttgcaatatt gaatcacatg ggggtttatt ttaaagaaga acccatccgt      60
gaacttcatc gcgcgcttga acgtctgaac ttccagattg tttacccgaa cgaccgtgac     120
gacttattaa aactgatcga aaacaatgcg cgtctgtgcg gcgttatttt tgactgggat     180
aaatataatc tcgagctgtg cgaagaaatt agcaaaatga acgagaacct gccgttgtac     240
gcgttcgcta atacgtattc cactctcgat gtaagcctga atgacctgcg tttacagatt     300
agcttctttg aatatgcgct gggtgctgct gaagatattg ctaataagat caagcagacc     360
actgacgaat atatcaacac tattctgcct ccgctgacta aagcactgtt taaatatgtt     420
cgtgaaggta aatatacttt ctgtactcct ggtcacatgg gcggtactgc attccagaaa     480
agcccggtag gtagcctgtt ctatgatttc tttggtccga ataccatgaa atctgatatt     540
tccatttcag tatctgaact gggttctctg ctggatcaca gtggtccaca caaagaagca     600
gaacagtata tcgctcgcgt ctttaacgca gaccgcagct acatggtgac caacggtact     660
tccactgcga acaaaattgt tggtatgtac tctgctccag caggcagcac cattctgatt     720
gaccgtaact gccacaaatc gctgaccac ctgatgatga tgagcgatgt tacgccaatc     780
tatttccgcc cgacccgtaa cgcttacggt attcttggtg gtatcccaca gagtgaattc     840
cagcacgcta ccattgctaa gcgcgtgaaa gaaacaccaa acgcaacctg gccggtacat     900
gctgtaatta ccaactctac ctatgatggt ctgctgtaca acaccgactt catcaagaaa     960
acactggatg tgaaatccat ccactttgac tccgcgtggg tgccttacac caacttctca    1020
ccgatttacg aaggtaaatg cggtatgagc ggtggccgtg tagaagggaa agtgatttac    1080
gaaacccagt ccactcacaa actgctggcg gcgttctctc aggcttccat gatccacgtt    1140
aaaggtgacg taaacgaaga aacctttaac gaagcctaca tgatgcacac caccacttct    1200
ccgcactacg gtatcgtggc gtccactgaa accgctgcgg cgatgatgaa aggcaatgca    1260
ggtaagcgtc tgatcaacgg ttctattgaa cgtgcgatca aattccgtaa agagatcaaa    1320
cgtctgagaa cggaatctga tggctggttc tttgatgtat ggcagccgga tcatatcgat    1380
acgactgaat gctggccgct gcgttctgac agcacctggc acggcttcaa aaacatcgat    1440
aacgagcaca tgtatcttga cccgatcaaa gtcaccctgc tgactccggg gatggaaaaa    1500
gacggcacca tgagcgactt tggtattccg ccagcatcg tggcgaaata cctcgacgaa    1560
catggcatcg ttgttgagaa aaccggtccg tataacctgc tgttcctgtt cagcatcggt    1620
atcgataaga ccaaagcact gagcctgctg cgtgctctga ctgactttaa acgtgcgttc    1680
gacctgaacc tgcgtgtgaa aaacatgctg ccgtctctgt atcgtgaaga tcctgaattc    1740
tatgaaaaca tgcgtattca ggaactggct cagaatatcc acaaactgat tgttcaccac    1800
aatctgccgg atctgatgta tcgcgcatt gaagtgctgc cgacgatggt aatgactccg    1860
tatgctgcat tccagaaaga gctgcacggt atgaccgaag aagtttacct cgacgaaatg    1920
gtaggtcgta ttaacgccaa tatgatcctt ccgtacccgc cggagttcc tctggtaatg    1980
ccgggtgaaa tgatcaccga agaaagccgt ccggttctgg agttcctgca gatgctgtgt    2040
gaaatcggcg ctcactatcc gggctttgaa accgatattc acggtgcata ccgtcaggct    2100
gatggccgct ataccgttaa ggtattgaaa gaagaaagca aaaaataa                 2148
```

<210> SEQ ID NO 3
<211> LENGTH: 17
<212> TYPE: DNA
<213> ORGANISM: Artificial Sequence
<220> FEATURE:
<223> OTHER INFORMATION: Primer (M13 Primer RV)

<400> SEQUENCE: 3
caggaaacag ctatgac                                                        17

<210> SEQ ID NO 4
<211> LENGTH: 19
<212> TYPE: DNA
<213> ORGANISM: Artificial Sequence
<220> FEATURE:
<223> OTHER INFORMATION: Primer (cadaf1)

<400> SEQUENCE: 4
ctaataagat caagcagac                                                      19

<210> SEQ ID NO 5
<211> LENGTH: 18
<212> TYPE: DNA
<213> ORGANISM: Artificial Sequence
<220> FEATURE:
<223> OTHER INFORMATION: Primer (cadaf2)

<400> SEQUENCE: 5
ctgacccacc tgatgatg                                                       18

<210> SEQ ID NO 6
<211> LENGTH: 18
<212> TYPE: DNA
<213> ORGANISM: Artificial Sequence
<220> FEATURE:
<223> OTHER INFORMATION: Primer (cadaf3)

<400> SEQUENCE: 6
tgacgtaaac gaagaaac                                                       18

<210> SEQ ID NO 7
<211> LENGTH: 18
<212> TYPE: DNA
<213> ORGANISM: Artificial Sequence
<220> FEATURE:
<223> OTHER INFORMATION: Primer (cadaf4)

<400> SEQUENCE: 7
cgaaatacct cgacgaac                                                       18

<210> SEQ ID NO 8
<211> LENGTH: 20
<212> TYPE: DNA
<213> ORGANISM: Artificial Sequence
<220> FEATURE:
<223> OTHER INFORMATION: Primer (cadaf5)

<400> SEQUENCE: 8
tgcataccgt caggctgatg                                                     20

<210> SEQ ID NO 9
<211> LENGTH: 20
<212> TYPE: DNA
<213> ORGANISM: Artificial Sequence
<220> FEATURE:
<223> OTHER INFORMATION: Primer (cadar1)

<400> SEQUENCE: 9
tcgaacgcac gtttgaagtc                                                     20

```
<210> SEQ ID NO 10
<211> LENGTH: 17
<212> TYPE: DNA
<213> ORGANISM: Artificial Sequence
<220> FEATURE:
<223> OTHER INFORMATION: Primer (M13 Primer M4)

<400> SEQUENCE: 10
gttttcccag tcacgac                                                   17

<210> SEQ ID NO 11
<211> LENGTH: 47
<212> TYPE: DNA
<213> ORGANISM: Artificial Sequence
<220> FEATURE:
<223> OTHER INFORMATION: Primer (v3i_r)

<400> SEQUENCE: 11
catgtgattc aatattgcaa taatgttcat ctacattcct ccttacg                  47

<210> SEQ ID NO 12
<211> LENGTH: 47
<212> TYPE: DNA
<213> ORGANISM: Artificial Sequence
<220> FEATURE:
<223> OTHER INFORMATION: Primer (v3i_f)

<400> SEQUENCE: 12
cgtaaggagg aatgtagatg aacattattg caatattgaa tcacatg                  47
```